United States Patent [19]

Vahlensieck et al.

[11] Patent Number: 4,824,982

[45] Date of Patent: Apr. 25, 1989

[54] METHOD FOR THE CLEAVAGE OF ORGANIC SILOXANES, AND PRODUCTS AND APPLICATIONS THEREOF

[75] Inventors: Hans-Joachim Vahlensieck, Wehr; Hans-Joachim Koetzsch, Rheinfelden, both of Fed. Rep. of Germany

[73] Assignee: Huels Troisdorf AG, Troisdorf Bez. Cologne, Fed. Rep. of Germany

[21] Appl. No.: 576,621

[22] Filed: Feb. 3, 1984

[30] Foreign Application Priority Data

Feb. 4, 1983 [DE] Fed. Rep. of Germany ....... 3303707

[51] Int. Cl.$^4$ ................................................ C07F 7/08
[52] U.S. Cl. .................................... 556/451; 556/462; 502/171; 502/172; 502/229; 44/76
[58] Field of Search .................... 556/462, 451; 44/76; 502/171, 172, 229

[56] References Cited

U.S. PATENT DOCUMENTS

| | | | |
|---|---|---|---|
| 2,421,653 | 6/1947 | Sauer | 260/607 |
| 2,529,496 | 11/1950 | Hughes | 44/69 |
| 3,065,252 | 11/1962 | Brown et al. | 556/451 |
| 3,101,361 | 8/1963 | Brown et al. | 556/451 X |
| 3,308,145 | 3/1967 | Lentz | 260/448.2 |
| 4,310,680 | 1/1982 | Kötzsch et al. | 556/453 |

FOREIGN PATENT DOCUMENTS

| | | | |
|---|---|---|---|
| 1167341 | of 0000 | Fed. Rep. of Germany | 556/454 UX |
| 2193049 | of 0000 | France | 454 UX/ |
| 914460 | of 0000 | United Kingdom | 556/454 UX |

Primary Examiner—Paul F. Shaver
Attorney, Agent, or Firm—Felfe & Lynch

[57] ABSTRACT

A method for the cleavage of organosiloxanes with chlorosilanes in the presence of ferric chloride and hydrogen chloride as catalysts resulting in chloroalkyl silanes or chloroaryl silanes, and organosiloxanes, which are characterized by one or more —O—Si—R$_3$ groups, (R=alkyl or aryl), which are directly bound to a silicon atom which in turn is bound either to the same grouping or to an alkyl or aryl moiety.

11 Claims, No Drawings

METHOD FOR THE CLEAVAGE OF ORGANIC SILOXANES, AND PRODUCTS AND APPLICATIONS THEREOF

BACKGROUND OF THE INVENTION

The subject of the present invention is a catalytic process for the cleavage of liquid organic disiloxanes with chlorosilanes with the simultaneous production of organic chlorosilanes of the general formula $R_3SiCl$, and of organic siloxanes of the general formula $R''_{4-n}Si(OSiR_3)_n$, wherein R represents identical or different alkyl or aryl moieties, and wherein R" represents H, alkyl moieties of 1 to 18 carbon atoms, or aryl moieties, both being able to be substituted by the group

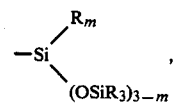

and represents the grouping

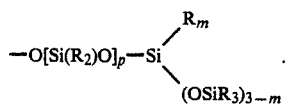

The previous work on this reaction principle has been described thus far by J. R. Elliot et al. in J. Amer. Chem. Soc. 74, 1853 sqq. (1952), M. G. Woronkov et al. in J. Obsh. Chim. 29 (1959), 1508–1514, and in Dokl. Akad. Nauk SSSR 227 (1976)(2), eng., 198–201, and in U.S. Pat. Nos. 3,065,252 (1962) and 3,101,361 (1963).

The average person skilled in the art learns from these works that both the few chlorosilanes tested and the siloxanes have quite different reactivities, but that generally the tendency is towards very slow reactions, and that the reaction as a rule remains incomplete, but at the same time not only momomeric but to some extent also polymeric siloxanes containing Si—Cl are formed. The yields of Si—Cl—free persilylated products obtained thus far are too low for economically profitable uses, although a whole series of such products are susceptible of significant applications. The problem therefore existed of finding for this process, which is known in itself, an embodiment making it possible to accelerate the reaction, block off possible secondary reactions, and increase the yields considerably.

A method has now been found for the cleavage of organodisiloxanes of the general formula $(R_3Si)_2O$, in which R represents identical or different, saturated or unsaturated alkyl moieties of 1 to 18 carbon atoms, substituted if desired by ester, halogen or aryl moieties, or represents aryl moieties substituted if desired with chlorosilanes of the general formula $$R'_{4-n}SiCl_n (n=2, 3 \text{ or } 4)$$

wherein R' represents H and/or R, these moieties also being able to be substituted by the group

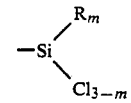

(m=0 or 1 or 2), or it represents the moiety of the formula

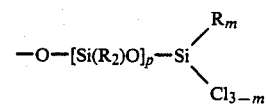

in which R has the same meaning as above and p can have a value of from 0 to 4, with the simultaneous production of organochlorosilanes of the general formula $R_3SiCl$ and of organosiloxanes of the general formula $R''_{4-n}Si(OSiR_3)_n$, in which R" is the same as R' and/or represents the grouping

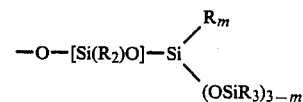

by performing the reaction in the presence of ferric chloride and catalytic amounts of hydrochloric acid.

This method offers a decided advance in regard to yield, product quality, and general usefulness, which was not to have been expected on the basis of the former state of knowledge.

The method of the invention is performed simply by mixing the siloxane component $(R_3Si)_2O$ with the chlorosilane component $R'_{4-n}SiCl_n$ and the ferric chloride catalyst, and starting the reaction by feeding into it a catalytic amount (0.05 to 1% by weight) of gaseous hydrogen chloride, and controlling the reaction by stirring and temperature control, by cooling or heating if necessary, until the mixture has ceased to react. It can be advantageous from time to time to restore the catalytic level of the hydrogen chloride.

If desired, catalytic amounts of 0.02–0.5 weight-percent of phosphorus trichloride and about 0.05 to 1 weight-percent of hydrogen chloride are added to the mixture toward the end of the reaction. Conventional methods of distillation are used for the separation of the chlorosilane and, if desired, of the siloxanes.

The ferric chloride catalyst is used in substance or as a solution of 1 to 15% by weight of anhydrous iron(III) chloride, preferably in ketones. It is used in concentrations of between 0.01% and 10% of the amount of siloxane used.

The reaction temperature is not critical. It can be any temperature from ambient to the boiling temperature of the reaction system. A temperature range between 20° and 55° C. is preferred, and it is advantageous to keep the temperature below the boiling temperature of the reaction system so as to avoid hydrogen chloride losses.

Atmospheric pressure conditions are preferred. But it is possible to work in a pressure range between 1 and 10 Bar, too.

A reactor equipped for stirring and with heating and cooling systems is preferred as the apparatus for the practice of the method of the invention.

Disiloxanes are used as starting substances of the general formula $(R_3Si)_2O$, especially hexamethyldisiloxane produced as waste in the synthesis of antibiotics; other examples are 1.2-divinyltetramethyldisiloxane, hexaethyldisiloxane, 1.2-di-3'-acetoxypropyltetramethyldisiloxane 1.2-dimethyltetraphenyldisiloxane, 1.2-di-tertiarybutyltetramethyldisiloxane, 1.2-bis-dodecyltetramethyldisiloxane and 1.2-di-2'-phenylethyltetramethyldisiloxane. It is a special advantage of the process of the invention that it can also operate with contaminated siloxanes such as, for example, siloxane containing solvents such as toluene or chloroform. Siloxanes containing amine are to be neutralized before use.

Chlorosilanes of many different kinds are used as starting substances of the general formula $R'_{4-n}SiCl_n$. Examples are: tetrachlorosilane, trichlorosilane, dichlorosilane, hexachlorodisiloxane, decachlorotetrasiloxane, methyltrichlorosilane, methylhydrogendichlorosilane, dimethyldichlorosilane, ethyltrichlorosilane, propyltrichlorosilane, isobutyltrichlorosilane, octyltrichlorosilane, octadecyltrichlorosilane, vinyltrichlorosilane, vinylmethyldichlorosilane, 1.2-bis-trichlorosilylethane, 1.2-bis-trichlorosilylethylene, allyltrichlorosilane, propenyltrichlorosilane, chloromethylmethyldichlorosilane, 2-chloroethylmethyldichlorosilane, 3-chloropropyltrichlorosilane, 1-trichlorosilyl-1,3-butadiene, propinyltrichlorosilane, phenyltrichlorosilane, phenylmethyldichlorosilane, diphenyldichlorosilane, tolyltrichlorosilane, cyclohexadienyltrichlorosilane, bis-trichlorosilylbenzenes, bis-trichlorosilylcyclohexenes etc. Mixtures of these compounds can also be used.

The moiety R' can accordingly represent any like or unalike moieties from the group, hydrogen, alkyl, aryl or alkenyl, and they can be substituted, preferably terminally, by a halogen or an

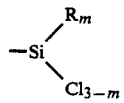

group. The moiety R' can also represent the grouping:

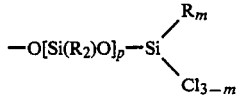

wherein m can be equal to 0 to 3, and p equal to 0 to 4.

In the catalyst system, the use in accordance with the invention of catalytic amounts of hydrogen chloride together with ferric chloride (solid or dissolved), in the above-given concentrations, is effective in the scope of the method of the invention.

It has furthermore proven advantageous to use as the catalyst in accordance with the invention ferric chloride in the form of its addition complex compounds with compounds containing oxo groups, such as ketones, aldehydes or carboxylic acid chlorides, together with a catalytic amount of hydrogen chloride. Ketones are preferred. Oxo compounds—preferably ketones in accordance with the invention—form solvates with ferric chloride, an example being $C_6H_5COCH_3 \cdot FeCl_3$ from acetophenone (cf. Beilstein 7, IV 619), these solvates being always present in the solution of ferric chloride in the ketones, as can be proven by the infrared spectra; they are prepared in accordance with the invention by the simple dissolution of ferric chloride in the corresponding ketone, in the cold.

Ketones which are suitable for these catalytic purposes in accordance with the invention are, for example, acetone, 2-butanone, 4-methyl-2-pentanone, mesityl oxide, acetophenone, dibenzalacetone, benzophenone, and cyclohexanone. The special advantage of the use of such ketone solvates lies in the considerable acceleration of the reaction which is thereby achieved.

It is particularly in the case of reaction mixtures in which the speed of the reaction decreases with the progress of the reaction that the phosphorus trichloride co-catalyst, in the above-named concentrations, is used additionally, in combination with catalytic amounts of hydrogen chloride, and, in accordance with the invention, toward the end of the reaction. The phosphorus trichloride addition in accordance with the invention then brings about a more rapid completion of the remainder of the transformation reaction that is still to be expected. Surprisingly, this additional catalytic effect in accordance with the invention does not take place if the phosphorus trichloride is added to the reaction mixture at the outset, with or without the ferric chloride/hydrogen chloride/ketone catalyst of the invention.

Substances prepared by the method of the invention are, for example, the siloxane compounds of the general formula $R''_{4-n}Si(OSiR_3)_n$, all obtainable from hexamethyldisiloxane, simultaneously with trimethylchlorosilane as a second product, which are listed herewith:

2.2.6.6-tetramethyl-4.4-bistrimethylsiloxy-2.4.6-trisila-3.5-dioxaheptane,
2.2.6.6-tetramethyl-4-trimethylsiloxy-2,4,6-trisila-3.5-dioxaheptane,
2.2.6.6-tetramethyl-2.4.6-trisila-3.5-dioxaheptane,
2.2.8.8-tetramethyl-4.4.6.6-tetrakis-trimethylsiloxy-2.4.6.8-tetrasila-3.5.7-trioxanonane,
2.2.4.6.6-pentamethyl-4-trimethylsiloxy-2.4.6-trisila-3.5-dioxaheptane,
2.2.4.4.6.6-hexamethyl-2.4.6-trisila-3.5-dioxaheptane,
2.2.6-trimethyl-4.4-bis-trimethylsiloxy-2.4-disila-3-oxaheptane,
2.2-dimethyl-4.4-bis-trimethylsiloxy-2.4-disila-3-oxadocosane,
2.2.6.6-tetramethyl-4-vinyl-4-trimethylsiloxy-2.4.6-trisila-3.5-dioxaheptane,
2.2.4.6.6-pentamethyl-4-vinyl-2.4.6-trisila-3.5-dioxaheptane,
2.2.9.9-tetramethyl-4.4.7.7-tetrakis-trimethylsiloxy-2.4.7.9-tetrasila-3.8-dioxadecane,
2.2.4.6.6-pentamethyl-4-chloromethyl-2.4.6-trisila-3.5-dioxaheptane,
2.2-dimethyl-4.4-bis-trimethylsiloxy-2.4-disila-3-oxaheptane,
2.2-dimethyl-4.4-bis-trimethylsiloxy-7-chloro-2.4-disilia-3-oxaheptane,
2.2-dimethyl-4.4-bis-trimethylsiloxy-2.4-disila-3-oxaoctadiene-(5.7)
2.2-dimethyl-4.4-bis-trimethylsiloxy-2.4-disila-3-oxaheptene-(6)
2.2.6.6-tetramethyl-4-phenyl-4-trimethylsiloxy-2.4.6-trisila-3.5-dioxaheptane,
2.2.4.6.6-pentamethyl-4-phenyl-2.4.6-trisila-3.5-dioxaheptane,
2.2.6.6-tetramethyl-4.4-diphenyl-2.4.6-trisila-3.5-dioxaheptane,
2.2.4.6.6-pentamethyl-4-p-bromophenyl-2.4.6-trisila-3.5-dioxaheptane, 2.2.6.6-tetramethyl-4-tolyl-4-trimethylsiloxy-2.4.6-trisila-3.5-dioxaheptane,
2.2.6.6-tetramethyl-4-cyclohexenyl-4-trimethylsiloxy-2.4.6-trisila-3.5-dioxaheptane,
2.2.6.6-tetramethyl-4-cyclohexadienyl-4-trimethylsiloxy-2.4.6-trisila-3.5-dioxaheptane,
Bis-(tris-trimethylsiloxy)silylbenzene isomers.

The following are additional examples of substances prepared by the method of the invention:

2.2.3.3.7.7.8.8-octamethyl-5-tert.butyldimethylsiloxy-3.5.7-trisila-4.6-dioxanonane and tert.butyldimethylchlorosilane from 1.2-ditert.butyltetramethyldisiloxane and trihlorosilane, 2.2.6.6-tetraphenyl-4.4-dimethyl-2.4.6-trisila-3.5-dioxaheptane and methyldiphenylchlorosilane from 1.2-dimethyltetraphenyldisiloxane and dimethyldichlorosilane, 1.5.5.9-tetraphenyl-3.3.7.7-tetramethyl-3.5.7-trisila-4.6-dioxanonane and dimethyl-2-phenylethylchlorosilane from 1.2-di-2-phenylethyltetramethyldisiloxane and diphenyldichlorosilane.

The chlorosilanes of the general formula $R_3SiCl$ produced in the reaction of the invention are valuable intermediates and end products for which applications exist in protective-group chemistry. The organosiloxanes of the general formula $R''_{4-n}Si(OSiR_3)_n$, some of them new, which can now be prpared in a simple and economical manner by the method of the invention, have a wide variety of valuable properties.

Organosiloxanes having a large proportion of branched, unsaturated and aromatic organosubstituents, which can be prepared by the method of the invention, are used to advantage as additives in heating and motor fuel oils, in concentrations between 0.05 and 0.8 weight-percent for keeping fuel gas and exhaust gas devices free of deposits caused by oil combustion, for making the combustion complete and thus increasing the energy yield, and for reducing the dangers of corrosion and atmospheric pollution involved in combustion processes.

Additional examples of applications are the use of such compounds, prepared by the method of the invention, as diffusion pump oils, such as for example the above-cited 2.2.6.6-tetraphenyl-4.4-dimethyl-2.4.6-trisila-3.5-dioxaheptane, as heat carrying liquids, and as conditioners for hydrophilic and hydrophobic phases.

The following examples will explain the invention, without, however, restricting it.

EXAMPLE 1

Preparation of 2.2.6.6-tetramethyl-4-trimethylsiloxy-2.4.6-trisila-3.5-dioxaheptane and trimethylchlorosilane from trichlorosilane and hexamethyldisiloxane in the presence of a ferric chloride and hydrogen chloride catalyst.

In a 6-liter multiple-neck flask with stirrer, reflux condenser, internal thermometer and an immersion capillary tube for the introduction of hydrogen chloride, 678 g (5 mol) of trichlorosilane and 2.500 g (15.4 mol) of hexamethyldisiloxane were mixed together at 18° C. After the addition of 350 mg of anhydrous iron-(III) chloride, with stirring, 2.5 g of hydrogen chloride was added, with stirring. The internal temperature then rose within 40 minutes due to self-heating, to 48° C. and, after another 45 minutes, began to decrease slowly.

After the heat effect had completely ended after about 4 hours total reaction time, 1,590 g of trimethylchlorosilane (yield 97.7% with respect to trichlorosilane) and 1,404 g of 2.2.6.6-tetramethyl-4-trimethylsiloxy-2.4.6-trisila-3.5-dioxaheptane (yield 94.8% with respect to trichlorosilane) of a $BP_{10}$ of 68° C. were obtained by distillation. Also, approximately 56 g of 1.1.2.2-tetrakis-trimethylsiloxydisiloxane was contained in the distillation residue.

EXAMPLE 2

Preparation of 2.2.3.3.7.7.8.8-octamethyl-5-tertiarybutyldimethylsiloxy-3.5.7-trisila-4.6-dioxanonane and tertiarybutyldimethylchlorosilane from trichlorosilane and 1.2-ditertiarybutyltetramethyldisiloxane in the presence of a ferric chloride, 2-propane and hydrogen chloride catalyst.

In a manner similar to Example 1, 542 g (4 mol) of trichlorosilane was mixed with an excess of 3450 g (14 mol) of 1.2-ditertiarybutyltetramethyldisiloxane at 20° C. After the addition of 10 ml of a 4% solution of ferric chloride in acetone, 3 g of hydrogen chloride was introduced. Within 10 minutes thereafter the internal temperature rose to 33° C. and after another 80 minutes it began to decrease again, slowly. After another 60 minutes, gas chromatography showed that the transformation rate had amounted to about 90%.

Immediately thereafter, 2 ml of phosphorus trichloride was added to the reaction mixture, and again 3 g of hydrogen chloride was introduced into it. Two hours later the entire reaction had ended. Distillation yielded 1728 g of tertiarybutyldimethychlorosilane (yield 95.6% with reference to trichlorosilane) and 1488 g of the previously unknown compound, 2.2.3.3.7.7.8.8-octamethyl-5-tertiarybutyldimethylsiloxy-3.5.7-trisila-4.6-dioxanonane (yield 88% with respect to trichlorosilane), with a melting point of 86° C.

Also recovered was 582 g of 1.2-ditertiarybutyltetramethyldisiloxane. The distillation residue contained approximately 130 g of 1.1.2.2-tetrakis-tertiarybutyldimethylsiloxydisiloxane.

EXAMPLE 3

Preparation of 2.2.6-trimethyl-4.4-bis-trimethylsiloxy-2.4-disila-3-oxaheptane and trimethylchlorosilane from isobutyltrichlorosilane and hexamethyldisiloxane in the presence of a catalyst consisting of ferric chloride, acetophenone and hydrogen chloride.

In a manner similar to Examples 1 and 2, the reaction of 766 g (4 mol) of isobutyltrichlorosilane with an excess of 2100 (13 mol) of hexamethyldisiloxane in the presence of 20 ml of a 2% solution of ferric chloride in acetophenone at 19° C. was started with 2 g of hydrogen chloride. After about one hour, the reaction mixture had warmed up to 34° C. After another hour, another 2 g of hydrogen chloride was introduced at 31° C. After a reaction time totaling 5 hours, gas chromatography indicated a reaction rate of about 94%, and the reaction was completed with the aid of 2 g of phosphorus trichloride and another 3 g of hydrogen chloride within 2 hours.

Distillation yielded 1274 g of trimethylchlorosilane (97.8% yield with respect to isobutyltrichlorosilane) plus 1322 g of the previously unknown 2.2.6-trimethyl-4.4-bistrimethylsiloxy-2.4-disila-3-oxaheptane (93.8% yield) having a $BP_1$ of 96° C., useful as a combustion additive.

EXAMPLE 4

Preparation of 2.2.6.6-tetramethyl-4-phenyl-4-trimethylsiloxy-2.4.6-trisila-3.5-dioxaheptane and trimethylchlorosilane from phenyltrichlorosilane and hexamethyldisiloxane in the presence of a catalyst consisting of ferric chloride, 4-methyl-2-pentanone and hydrogen chloride.

In a manner similar to Examples 1 and 2, the reaction of 846 g (4 mol) of phenyltrichlorosilane with 2020 g (12.5 mol) of hexamethyldisiloxane was started at 20° C. with 3 g of hydrogen chloride in the presence of 50 ml of a 1% solution of ferric chloride in 4-methyl-2-pentanone. The temperature rose in 25 minutes to 41° C. 3 g of hydrogen chloride was introduced every 2 hours. After 5 hours, the reaction rate amounted to about 90%, and the reaction was completed in 3 hours by the addition of 2 g of phosphorus trichloride and 3 g of hydrogen chloride. Distillation yielded 1289 g of trimethylchlorosilane (99% yield) and 1403 g of 2.2.6.6-tetramethyl-4-phenyl-4-trimethylsiloxy-2.4.6-trisila-3.5-dioxaheptane (94.2% yield) having a $BP_1$ of 105° C.

EXAMPLE 5

Persilylation of a mixture consisting of 58% of 3-chloropropyltrichlorosilane, 36% of propyltrichlorosilane and about 6% of 2-methylpentyltrichlorosilane.

In a manner similar to Examples 1 and 2, 1 kg of the above mixture was brought to a reaction with 2.5 kg of hexamethyldisiloxane in the presence of 50 ml of a 1% solution of ferric chloride in 4-methyl-2-pentanone and 3 g of hydrogen chloride. The reaction mixture warmed within 25 minutes from 19° C. to 37° C. The reaction was continued as in Example 4. Distillation through a Sulzer column yielded 1.59 kg of trimethylchlorosilane (97.7% yield with respect to silicon chloride input), 514 g (84%) of 2.2-dimethyl-4.4-bis-trimethylsiloxy-2.4-disila-3-oxaheptane ($BP_1$ 70° C.) and 967 g (89%) of 2.2-dimethyl-4.4-bis-trimethylsiloxy-7-chloro-2.4-disila-3-oxaheptane ($BP_1$ 84° C.).

A fraction of 184 g which passed over at a $BP_1$ of 131° C. to 154° C. contained approximately 100 g of 2.2.6-trimethyl-4.4-bis-trimethylsiloxy-2.4-disila-3-oxa-decane. The above-named siloxane end products are substances unknown heretofore. They are useful as combustion additives.

EXAMPLE 6

Persilylation of a mixture having a silicon chloride content of about 59% consisting of about 25% of phenyltrichlorosilane, about 50% of bis-trichlorosilylbenzene isomers, about 10% of 1-trichlorosilyl-1.3-butadiene, about 10% of vinyltrichlorosilane, and others.

In a manner similar to Example 4, 900 g of the above mixture was brought to reaction with 3.2 kg of hexamethyldisiloxane containing 20% toluene, using 100 ml of catalyst solution. The reactor temperature rose within 6 minutes from 21° C. to 54° C. After 4 hours of reaction, the process was continued as in Example 4, with 1 ml of phosphorus trichloride. Distillation yielded 1620 g of trimethylchlorosilane in a virtually quantitative yield. The silylation product of the starting chlorosilanes, freed of toluene and 4-methyl-2-pentanone, was filtered through aluminum oxide. It contained less than 20 ppm of residual chlorine. The silylation products of the bis-trichlorosilylbenzene isomers and of 1-trichlorosilyl-1.3-butadiene are formerly unknown substances. Practical experiment proved their special usefulness as combustion additives in a concentration of 0.8% in heating and motor fuel oils.

EXAMPLE 7

Preparation of the diffusion pump oil, 2.2.6.6-tetraphenyl-4.4-dimethyl-2.4.6-trisila-3.5-dioxaheptane and methyldiphenylchlorosilane from 1.2-dimethyltetraphenyldisiloxane and dimethyldichlorosilane.

In a manner similar to Example 4, 387 g (3 mol) of dimethyldichlorosilane and 2476 g (6 mol) of 1.2-dimethyltetraphenyldisiloxane were reacted in the presence of 25 ml of an 8% solution of ferric chloride in mesityl oxide with heating to 75° C., and with the addition of 3 g of hydrogen chloride every 2 hours (using a total of 12 g of HCl). 8 hours later the reaction rate was about 90% and the reaction was terminated within 3 hours by the addition of 2 ml of phosphorus trichloride and another 3 g of hydrogen chloride.

Vacuum distillation through a Sulzer column yielded 1280 g (98% yield) of methyldiphenylchlorosilane, $BP_1$ 128° C., and 1340 g (92% yield) of 2.2.6.6-tetraphenyl-4.4-dimethyl-2.4.6-trisila-3.5-dioxaheptane, $BP_{0.2}$ 228° C.

EXAMPLE 8

Preparation of 2.2.8.8-tetramethyl-4.4.6.6-tetrakis-trimethylsiloxy-2.4.6.8-tetrasila-3.5.7-trioxanonane and trimethylchlorosilane.

In a mannr similar to Example 1, 570 g (2 mol) of hexachlorodisiloxane and 2.84 kg of hexamethyldisiloxane containing 20% toluene were brought to reaction in the presence of 20 ml of a 2% solution of ferric chloride in 4-methyl-2-pentanone at 22° C., with 3 g of hydrogen chloride. After about 30 minutes the temperature reached 30° C. and decreased slowly thereafter over a period of 8 hours. Every 2 hours, 3 g of hydrogen chloride was introduced. After 8 hours the reaction rate amounted to about 96%, and the reaction was completed within 3 hours by the addition of 1 kg of phosphorus trichloride and another 3 g of hydrogen chloride. Distillation yielded 1300 g (virtually quatitative yield). After the evaporation of residual hexamethyldisiloxane and toluene in the rotary evaporator, 1200 g (approximately 99% yield) of silylation product was obtained. The substance softens at 234° C. and has a pressure-related oil point with good lubricant properties.

EXAMPLE 9

Persilylation of tetrachlorosilane with hexamethyldisiloxane.

In a manner similar to Example 8, 850 g (5 mol) of tetrachlorosilane was reacted with 3.4 kg (about 21 mol) of hexamethyldisiloxane. The temperature initially rose to 47° C.

By distillation, 2150 g of trimethylchlorosilane (virtually quantitative yield) and 1800 g (93.5% yield) of 2.2.6.6-tetramethyl-4.4-bis-trimethylsiloxy-2.4.6-trisila-3.5-dioxaheptane, $BP_{10}$ 87° C. The distillation residue of approximately 80 g consisted mainly of 2.2.8.8-tetramethyl-4.4.6.6-tetrakis-trimethylsiloxy-2.4.6.8-tetrasila-3.5.7-trioxanone.

It will be understood that the specification and examples are illustrative but not limitative of the present invention and that other embodiments within the spirit and scope of the invention will suggest themselves to those skilled in the art.

We claim:
1. A method for the cleavage of organodisiloxanes of the general formula $(R_3Si)_2O$ in which R represents like or different saturated or unsaturated alkyl moieties, substituted if desired by ester, halogen or aryl moieties, and having 1 to 18 carbon atoms, or it represents aryl moieties substituted, if desired, with halogen or alkyl, with chlorosilanes of the general formula $R'_{4-n}SiCl_n (n=2, 3 \text{ or } 4)$ wherein R' represents H and/or R, these moieties being also able to be substituted by the group

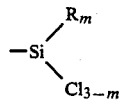

(m=0 or 1 or 2), or it represents the moiety of the formula

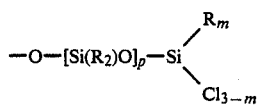

in which R has the same meaning as above and p can be equal to 0 to 4, with the simultaneous production of organochlorosilanes of the general formula $R_3SiCl$ and of organosiloxanes of the general formula $R''_{4-n}Si(OSiR_3)_n$, in which R'' is the same as R' and/or represents the grouping

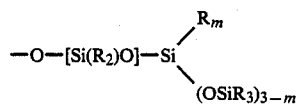

wherein the reaction is performed in the presence of ferric trichloride and catalytic amounts of hydrogen chloride.

2. The method of claim 1, wherein the ferric chloride is dissolved or suspended in organic solvents containing oxo groups.

3. The method of claim 1, wherein a catalytic amount of phosphorus trichloride is added following the initiation of the reaction and prior to its termination.

4. The method of claim 1, wherein the two starting components are used in such a ratio that the amount of siloxane is at least equivalent to one of the Si-bound chlorine atoms.

5. The method of claim 2, wherein the ferric chloride catalyst is used in substance or as a solution of 1–15 weight-percent of organic compounds carrying anhydrous iron(III) chloride in oxo groups, preferably in ketones, in a ferric chloride concentration with respect to the total mixture of 0.01 to 10 weight-percent.

6. The method of claim 1, wherein after mixing the organodisiloxane and chlorosilane and the catalyst, the reaction is started by the introduction of a catalytic amount of hydrogen chloride, preferably 0.05 to 1 weight-percent of HCl with respect to the total mixture.

7. The method of claim 3, wherein the phosphorus trichloride is used in amounts between 0.02 and 0.5 weight-percent, with respect to the total mixture.

8. The method of claim 2, wherein the organic solvents are ketones, aldehydes and carboxylic acid chlorides.

9. The method of claim 2, wherein the organic solvents are acetone, 2-butanone, 4-methyl-2-pentanone, mesityl oxide, acetophenone, dibenzylacetone, benzophenone and cyclohexanone.

10. A combustion additive for heating and/or motor fuel oils comprising a compound of the general formula $R''_{4-n}Si(OSiR_3)_n$ wherein R represents like or different saturated or unsaturated alkyl moieties, substituted if desired by ester, halogen or aryl moieties, and having 1 to 18 carbon atoms, or it represents aryl moieties substituted, if desired, with halogen or alkyl, and R'' is H and/or R and/or represents the grouping

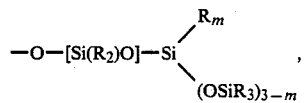

n=2, 3 or 4 and m=0, 1 or 2.

11. A catalyst system consisting essentially of iron(III) chloride dissolved in a liquid ketone with hydrogen chloride.

* * * * *